US012697452B2

(12) United States Patent
Kim

(10) Patent No.: US 12,697,452 B2
(45) Date of Patent: Aug. 4, 2026

(54) TRACHEAL INTUBATION GUIDE APPARATUS AND TRACHEAL INTUBATION GUIDE KIT COMPRISING SAME

(71) Applicant: Seoul National University Hospital, Seoul (KR)

(72) Inventor: Dae Kon Kim, Seongnam-Si (KR)

(73) Assignee: Seoul National University Hospital, Seoul (KR)

( * ) Notice: Subject to any disclaimer, the term of this patent is extended or adjusted under 35 U.S.C. 154(b) by 438 days.

(21) Appl. No.: 18/018,500

(22) PCT Filed: Jul. 30, 2021

(86) PCT No.: PCT/KR2021/009990
§ 371 (c)(1),
(2) Date: Jan. 27, 2023

(87) PCT Pub. No.: WO2022/025712
PCT Pub. Date: Feb. 3, 2022

(65) Prior Publication Data
US 2023/0372652 A1     Nov. 23, 2023

(30) Foreign Application Priority Data

Jul. 31, 2020     (KR) ......................... 10-2020-0096290

(51) Int. Cl.
*A61B 1/267*         (2006.01)
*A61B 1/00*          (2006.01)
*A61M 16/04*         (2006.01)
(52) U.S. Cl.
CPC ..... *A61M 16/0488* (2013.01); *A61B 1/00135* (2013.01); *A61B 1/267* (2013.01)

(58) Field of Classification Search
CPC ....... A61B 1/267–2676; A61M 16/0488–0497
See application file for complete search history.

(56) References Cited

U.S. PATENT DOCUMENTS 4,527,553 A *  7/1985  Upsher .............. A61B 1/00165
                                                        600/199
5,038,766 A *  8/1991  Parker .............. A61M 16/0488
                                                        2/908

(Continued)

FOREIGN PATENT DOCUMENTS

JP           2706567 B2     1/1998
JP        2004-523306 A     8/2004

(Continued)

*Primary Examiner* — Eduardo C Robert
*Assistant Examiner* — Steven J Cotroneo
(74) *Attorney, Agent, or Firm* — Jackson Walker LLP

(57)            ABSTRACT

Disclosed are a tracheal intubation guide apparatus and a tracheal intubation guide kit comprising same, wherein the tracheal intubation guide apparatus comprises a longitudinally curved cylindrical case capable of being inserted into an oral cavity, the case has an endotracheal tube insertion hole on a proximal side, an endotracheal tube discharge hole on a distal side, and a longitudinally curved tracheal intubation guide passage connecting the endotracheal tube insertion hole and the endotracheal tube discharge hole, one side of the distal end of the case is provided with a laryngeal cover clasp protruding from the case, the other side of the distal end of the case is provided with an esophageal insertion prevention plate protruding farther from the case than the laryngeal cover clasp to prevent insertion into the esophagus, and the endotracheal tube discharge hole is located in an area between the laryngeal cover clasp and the esophageal insertion prevention plate.

3 Claims, 7 Drawing Sheets

(56)     References Cited

U.S. PATENT DOCUMENTS

| | | | | |
|---|---|---|---|---|
| 5,174,283 | A | * | 12/1992 | Parker ............... A61M 16/0409<br>128/207.14 |
| 5,498,231 | A | * | 3/1996 | Franicevic ............. A61B 1/267<br>128/207.14 |
| 5,720,275 | A | * | 2/1998 | Patil .................. A61M 16/0418<br>128/207.14 |
| 5,743,254 | A | * | 4/1998 | Parker ............... A61M 16/0495<br>128/207.14 |
| 7,866,314 | B2 | * | 1/2011 | Isenberg ........... A61B 1/00165<br>128/207.14 |
| 2006/0264979 | A1 | | 11/2006 | Shepard |
| 2010/0249639 | A1 | * | 9/2010 | Bhatt .................... A61B 5/395<br>128/207.14 |
| 2020/0029800 | A1 | * | 1/2020 | Matus ............... A61B 1/00147 |
| 2021/0023320 | A1 | * | 1/2021 | Yi ........................ A61B 1/2676 |
| 2022/0355053 | A1 | * | 11/2022 | Alonso Babarro ... A61M 16/06 |

FOREIGN PATENT DOCUMENTS

| | | | | | |
|---|---|---|---|---|---|
| KR | 10-1724973 | B1 | | 4/2017 | |
| KR | 10-1789171 | B1 | | 10/2017 | |
| KR | 10-2019-0108376 | A | | 9/2019 | |
| WO | WO-2019177383 | A1 | * | 9/2019 | ........ A61M 16/0418 |

\* cited by examiner

TRACHEAL INTUBATION GUIDE APPARATUS AND TRACHEAL INTUBATION GUIDE KIT COMPRISING SAME

TECHNICAL FIELD

The present invention relates to a tracheal intubation guide apparatus and a tracheal intubation guide kit comprising the tracheal intubation guide apparatus. Specifically, the present invention relates to a tracheal intubation guide apparatus and a tracheal intubation guide kit comprising the tracheal intubation guide apparatus which enable tracheal intubation to be performed without insertion into the esophagus when an endotracheal tube is inserted even in a blind state with no sight of a trachea, allow easy assembly, and allow easy disassembly and removal of the corresponding apparatus to be performed after endotracheal tube intubation.

BACKGROUND ART

Out-of-hospital cardiac arrest (hereinafter, OHCA) is a principal issue in sociology of health experienced by 420,000 people annually, for example in the U.S., with a survival rate of only 10.4%. When a paramedic arrives at a corresponding site following a report of a patient suffering OHCA and performs cardiopulmonary resuscitation (CPR), securing of the trachea is very important, and endotracheal intubation (hereinafter, ETI) is particularly important to secure the trachea.

However, despite the importance of ETI, endotracheal intubation skills are hard to develop and requires many experiences, and there is a concern that failure of the skill can harm a patient. In addition, a delay in CPR for ETI can rather worsen the patient's prognosis.

Hence, a paramedic or the like inexperienced in ETI at emergency scenes has a tendency to prefer insertion of a supraglottic airway device (SAD) to the ETI.

However, although insertion can be easily performed by a supraglottic airway method, the appropriate insertion into the trachea is failed in many cases due to dislodgement, esophageal insertion, or the like, making it difficult to efficiently secure the trachea. In addition, even though the ETI is difficult to perform, the ETI is a gold-standard skill in securing the trachea, and thus to attempt ETI as many times as possible increases a possibility of a patient's good prognosis.

A guide apparatus for endotracheal intubation (for example, Patent Literature 1) is available in the related art; however, it is still difficult to easily secure a trachea without esophageal insertion in a blind state where the location of the trachea is not viewed.

Further, the guide apparatus in the related art is not removed after the endotracheal intubation, and thus a problem arises in that the guide apparatus interferes with another treatment or the like.

BACKGROUND ART LITERATURE

Patent Literature

1. Korean Patent Registration No. 1789171

DISCLOSURE

Technical Problem

According to one aspect of the present invention, there are provided a tracheal intubation guide apparatus and a tracheal intubation guide kit comprising the tracheal intubation guide apparatus which enable tracheal intubation to be performed without insertion into the esophagus whenever an endotracheal tube (hereinafter, E-tube) is inserted even in a blind state with no sight of a trachea during insertion of the E-tube such that even an operator such as an inexperienced paramedic can simply perform ETI.

According to another aspect of the present invention, there are provided a tracheal intubation guide apparatus and a tracheal intubation guide kit comprising the tracheal intubation guide apparatus which can be easily assembled and disassembled such that the guide apparatus can be easily disassembled to be removed after guiding an E-tube.

Solution to Problem

According to exemplary embodiments of the present invention, there is provided a tracheal intubation guide apparatus including: a longitudinally curved cylindrical case capable of being inserted into an oral cavity. The case has an endotracheal tube insertion hole on a proximal side, an endotracheal tube discharge hole on a distal side, and a longitudinally curved tracheal intubation guide passage connecting the endotracheal tube insertion hole and the endotracheal tube discharge hole. One side of the distal end of the case is provided with a laryngeal cover clasp protruding from the case, and the other side of the distal end of the case is provided with an esophageal insertion prevention plate protruding farther from the case than the laryngeal cover clasp to prevent insertion into the esophagus. The endotracheal tube discharge hole is located in an area between the laryngeal cover clasp and the esophageal insertion prevention plate.

According to the other exemplary embodiments of the present invention, there is provided a tracheal intubation guide kit including: the above-described tracheal intubation guide apparatus; and a manual (instructions) for using the tracheal intubation guide apparatus. The manual includes instructions for an operator to put and fix the tracheal intubation guide apparatus in an oral cavity of an operation subject, pass an endotracheal tube along the tracheal intubation guide passage of the tracheal intubation guide apparatus, and then decouple at least a first case body from a second case body of the tracheal intubation guide apparatus.

Advantageous Effects of the Invention

In a case of using a tracheal intubation guide apparatus of exemplary embodiments of the present invention, E-tube intubation into a trachea can be performed even in a blind state such that a possibility of wrong insertion into an esophagus is reduced and the trachea can be easily and reliably secured. Hence, in a situation where securing of the trachea is important at an emergency scene, an emergency room, an operating room, an intensive care unit, or the like, an ETI attempt barrier of an operator can be lowered and the ETI can be easy to attempt. In particular, a procedure of securing the trachea can be performed in a prehospital state.

In addition, according to the tracheal intubation guide apparatus of the exemplary embodiments of the present invention, since a first case body and a second case body are coupled to each other by a magnet, and a handle portion is coupled to the first case body and the second case body by screw coupling, the guide apparatus can be easily disassembled and removed after guiding the E-tube. Hence, no foreign matter is present in an oral cavity after endotracheal intubation, and thus a procedure such as aspirate suction is easy to perform.

In this regard, a tracheal intubation guide apparatus in the related art can perform a guide function only when the apparatus is kept placed in an oral cavity, and thus the guide apparatus interferes with aspirate suction, whereas the tracheal intubation guide apparatus of the exemplary embodiments of the present invention does not cause such a problem.

On the other hand, according to the tracheal intubation guide apparatus of the exemplary embodiments of the present invention, tooth clasps 211 and 221 are placed to have a centerline thereof located between 31st and 41st teeth of an operation subject, and thus an exit edge on a distal side of a tracheal intubation guide passage H can be placed immediately in the front of an entrance of the trachea. Hence, simply pushing in the endotracheal tube enables ETI to be easily performed.

DESCRIPTION OF REFERENCE NUMBERS

Figure 1A:
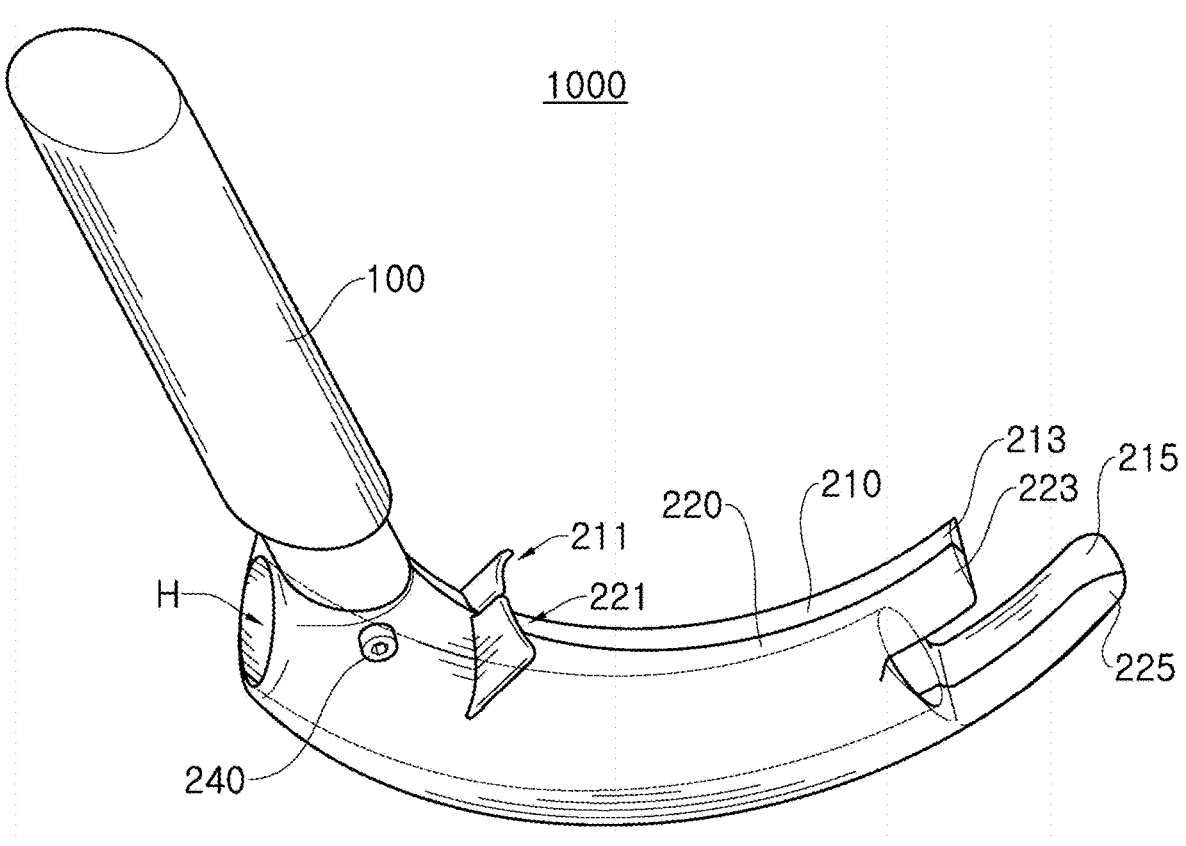
FIG. 1A is a perspective view illustrating a tracheal intubation guide apparatus according to an example of the present invention.

1000: Tracheal intubation guide apparatus
100: Handle
110: Screw through-hole
210: First case body
220: Second case body
211, 221: Tooth clasp
213, 223: Laryngeal cover clasps
215, 225: Esophageal insertion prevention plate
217, 227: Handle coupler
240: Screw
H: Guide passage
M: Magnet

MODE FOR INVENTION

Hereinafter, embodiments of the present invention will be described with reference to the drawings. Hereinafter, the following description is provided with reference to examples illustrated in the drawings; however, the examples are described as exemplary examples, and thus the technical ideas and the key configurations and actions of the present invention are not limited thereto.

In this specification, upper and lower parts, upper and lower sides, or right and left sides are to be construed as relative positional concepts. For example, left and right sides are to be construed to be referred to as right and left sides, respectively, depending on a viewing direction.

In this specification, to be used in assembled and disassembled states means not only that a tracheal intubation guide apparatus can be used by assembling configurational parts of the corresponding apparatus, but also that the corresponding tracheal intubation guide apparatus can be used by being disassembled in a state of being located in an oral cavity after E-tube intubation. In this respect, the configurational parts are fastened such that the tracheal intubation guide apparatuses of the exemplary embodiments of the present invention can be easily disassembled and assembled.

Figure 1B:
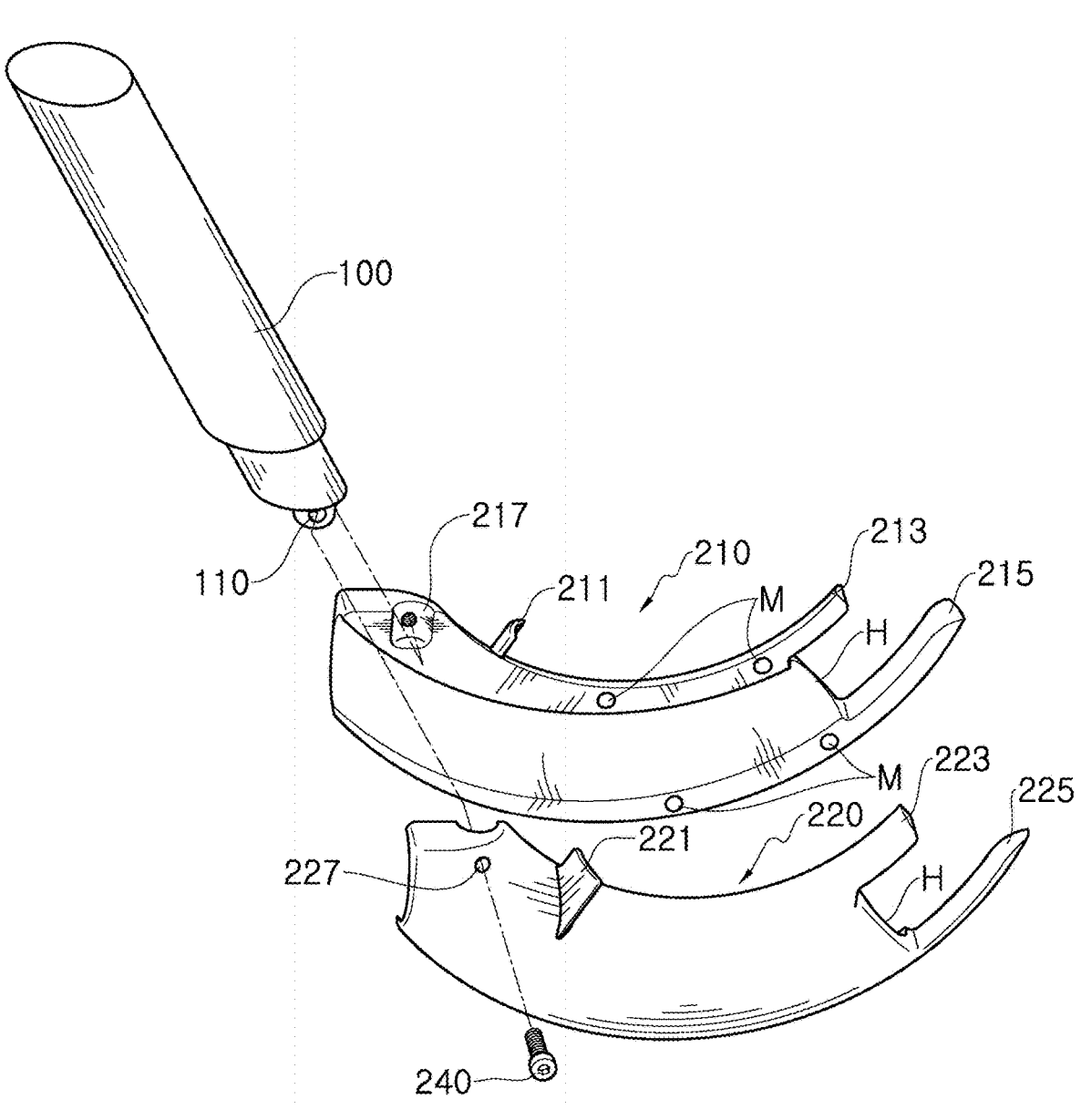
FIG. 1B is an exploded perspective view illustrating the tracheal intubation guide apparatus according to the example of the present invention.

FIG. 1A is a perspective view illustrating the tracheal intubation guide apparatus according to an example of the present invention, and FIG. 1B is an exploded perspective view illustrating the tracheal intubation guide apparatus according to the example of the present invention.

As illustrated in FIGS. 1A and 1B, a tracheal intubation guide apparatus 1000 according to the example includes a longitudinally curved cylindrical case capable of being inserted into an oral cavity.

As illustrated in FIG. 1 and FIG. 2 to be described below, the case can be curved to have a downward curve formed from a case proximal side to a case center and an upward curve from the case center to a case distal side so as to be suitable for entering the trachea after the case is inserted into the oral cavity.

The case can have a first case body 210 forming a right half (right side, when viewed from the distal side of the case) of the case and a second case body 220 forming a left half (left side, when viewed from the distal side of the case) of the case, and the first case body and the second case body can be coupled to each other by one or more magnets M. Here, the first case body and the second case body can be symmetrical to each other.

Specifically, the configurational parts are to be fastened such that the tracheal intubation guide apparatuses of the exemplary examples of the present invention can be disassembled and assembled.

First, the case of the tracheal intubation guide apparatus has a configuration in which the first case body 210 forming the right half of the case and the second case body 220 forming the left half of the case are fastened to be coupled to and decoupled from each other.

In the example, the first case body 210 and the second case body 220 can be fastened to each other by a fastening means, such as above-described one or more magnets M, which enable decoupling and coupling to be easily performed. For example, one of coupling surfaces of the first case body 210 and the second case body 220 can have a protruding portion, the other coupling surface thereof can have an accommodation portion which accommodates the protruding portion, and thus fastening and separation can be performed by inserting and pulling the protruding portion into and out of the accommodation portion.

The case formed by coupling the first case body 210 and the second case body 220 to each other has an endotracheal tube insertion hole on the proximal side of the case, an endotracheal tube discharge hole on the distal side of the case, and a longitudinally curved tracheal intubation guide passage H connecting the endotracheal tube insertion hole and the endotracheal tube discharge hole.

One side of the distal end of the case is provided with laryngeal cover clasps 213 and 223 protruding from the case. When the tracheal intubation guide apparatus according to the example enters along a tongue, the laryngeal cover clasps 213 and 223 are located between an epiglottis and a base of the tongue. As will be described below, when tooth clasps 211 and 221 can be clasped between two teeth at a center of a mandible of an operation subject, the tracheal intubation guide apparatus can be placed at an appropriate location in the oral cavity. Subsequently, when the tracheal intubation guide apparatus is lifted toward the sky, the laryngeal cover clasps 213 and 223 clasped on the epiglottis are pushed upward due to the anatomy and fulfill a function of pushing (opening) the epiglottis and exposing the trachea.

In addition, the other side of the distal end of the case is provided with esophageal insertion prevention plates 215 and 225 protruding farther from the case than the laryngeal cover clasps 213 and 223 to prevent insertion into the esophagus.

The discharge hole of the tracheal intubation guide passage H is located in an area between the laryngeal cover clasps 213 and 223 and the esophageal insertion prevention plates 215 and 225. Hence, the E-tube passing through the corresponding guide passage H easily enters the trachea in a state where the epiglottis is pushed upward to be opened by the laryngeal cover clasps 213 and 223 and in a state where the esophageal insertion prevention plates 215 and 225 block entry into the esophagus.

The tracheal intubation guide apparatus can further include the tooth clasps 211 and 221 on one side of the proximal side of the case.

Figure 3:
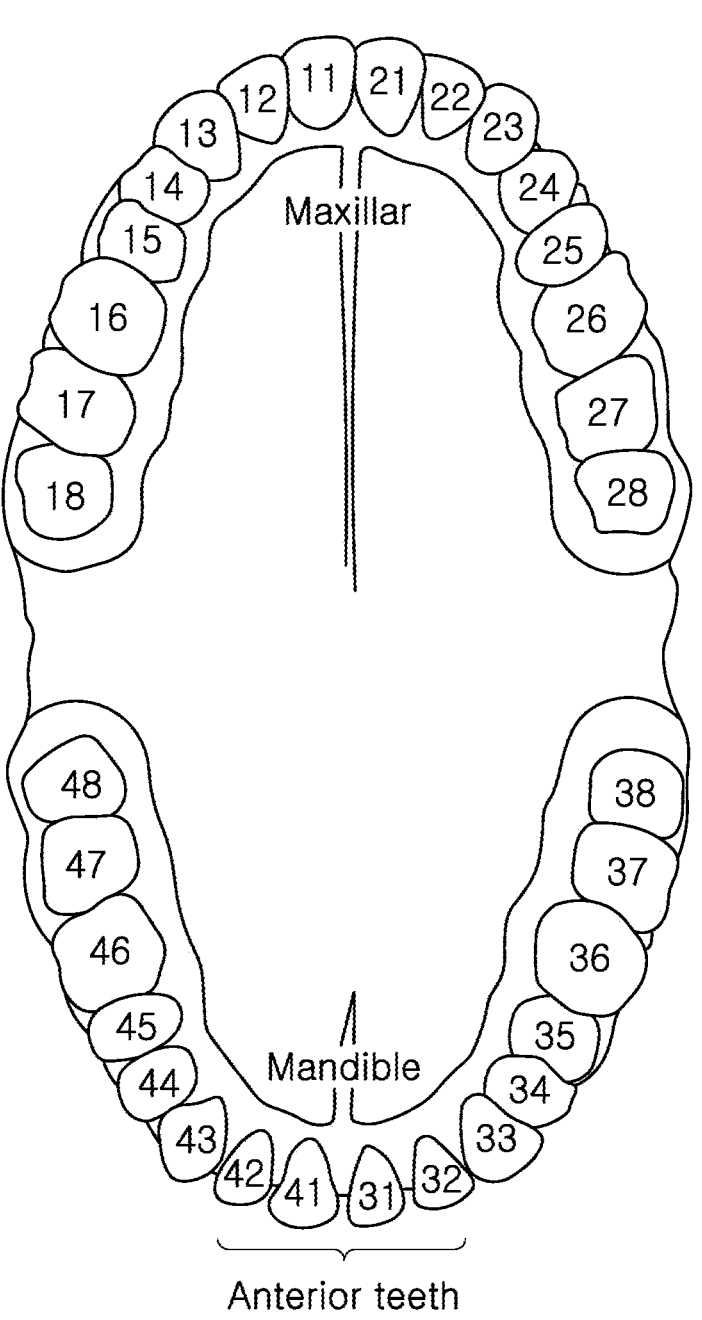
FIG. 3 is a schematic view illustrating human tooth numbers.

The tooth clasps 211 and 221 are to be clasped between two teeth, that is, 31st and 41st teeth (refer to FIG. 3), at the center of the mandible of the operation subject when the tracheal intubation guide apparatus is provided into the oral cavity of the operation subject. As described above, the tooth clasps 211 and 221 can be clasped between the 31st and 41st teeth, thereby aiding the positioning of an appropriate start location of the tracheal intubation guide apparatus.

For example, when an operation subject such as a patient is lying down facing a ceiling and the neck is positioned straight, the tooth clasps 211 and 221 are placed to have a centerline thereof located between the 31st and 41st teeth of the operation subject so that an exit edge on a distal side of the tracheal intubation guide passage H can be placed immediately in the front of an entrance of the trachea. Hence, simply pushing in the endotracheal tube enables ETI to be easily performed.

The tracheal intubation guide apparatus can further include a handle 100 that is coupled to the case.

As described above, the configurational parts are to be fastened such that the tracheal intubation guide apparatuses of the exemplary examples of the present invention can be disassembled and assembled. Hence, not only the first case body 210 and the second case body 220 described above are to be easily decoupled from and coupled to each other, but also the handle 100 is to be easily decoupled and coupled.

In this respect, the handle 100, the first case body 210, and the second case body 220 of the tracheal intubation guide apparatus can be fastened to be coupled to and decoupled from each other at a handle coupler by one fastening means.

For example, in the example, the handle 100 has a screw through-hole 110, and the screw through-hole 110 enables the first case body 210 and the second case body 220 to be coupled to each other at handle couplers 217 and 227 by using a screw 240.

Here, the handle 100 and the handle couplers 217 and 227 are positioned on a rear surface side of the tooth clasps 211 and 221 provided on the proximal side of the case.

Figure 2A:
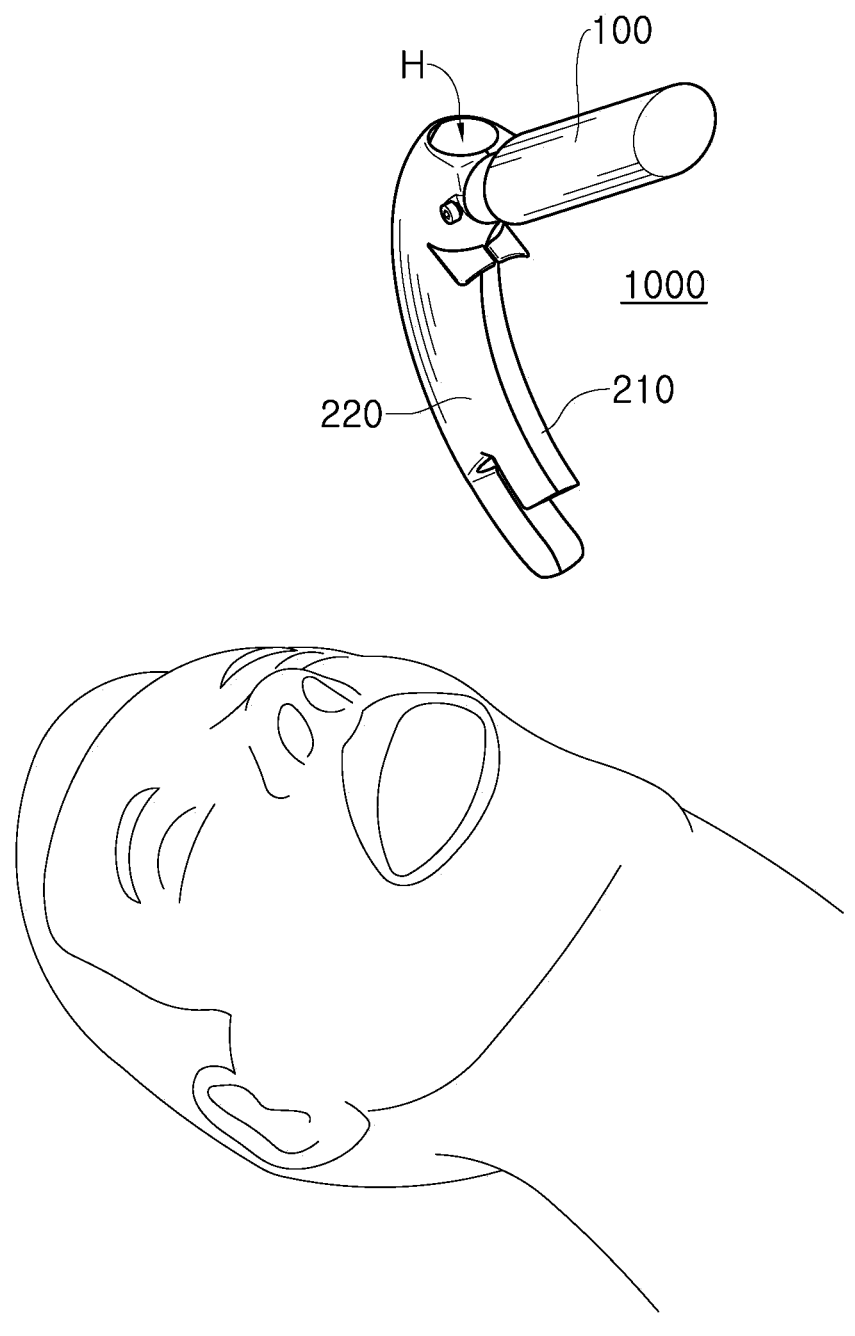
FIG. 2A is a schematic view illustrating a state before the tracheal intubation guide apparatus according to the example of the present invention is provided to an operation subject.
Figure 2B:
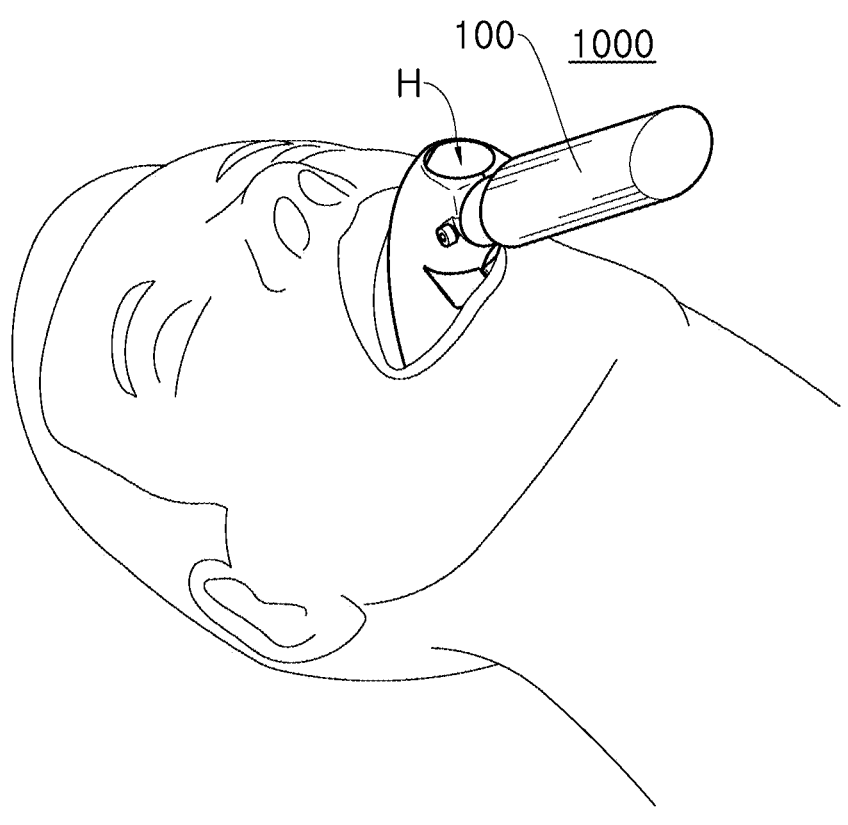
FIG. 2B is a schematic view illustrating a state where the tracheal intubation guide apparatus according to the example of the present invention is provided into an oral cavity of the operation subject.
Figure 2C:
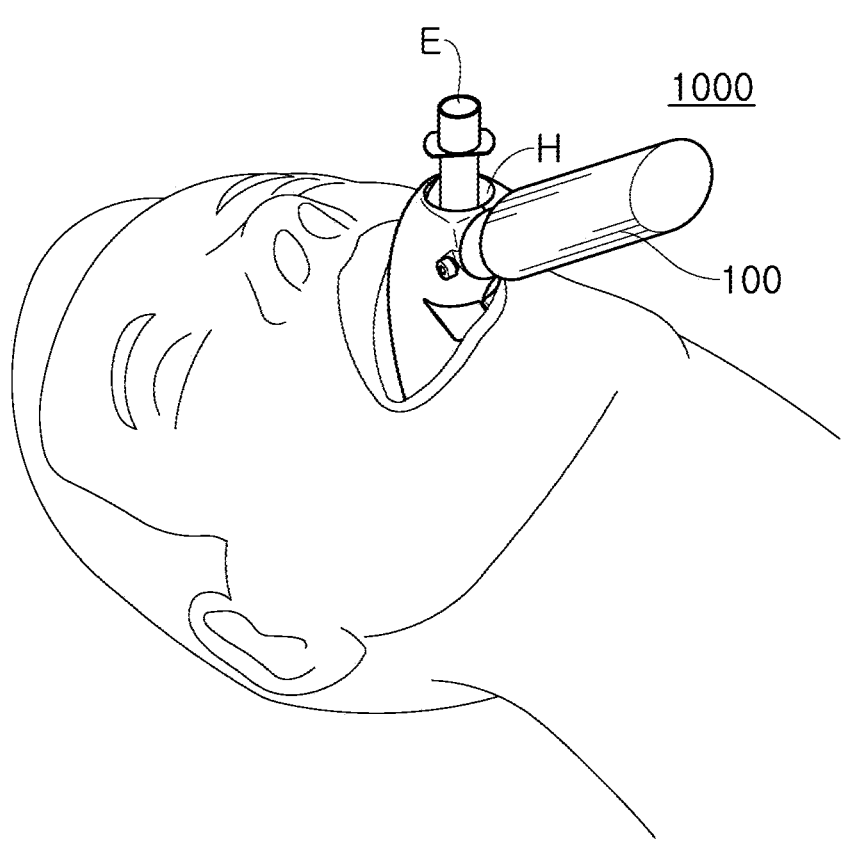
FIG. 2C is a schematic view illustrating a state where the tracheal intubation guide apparatus according to the example of the present invention is provided into the oral cavity of the operation subject and then an E-tube is provided through a tracheal intubation guide passage.
Figure 2D:
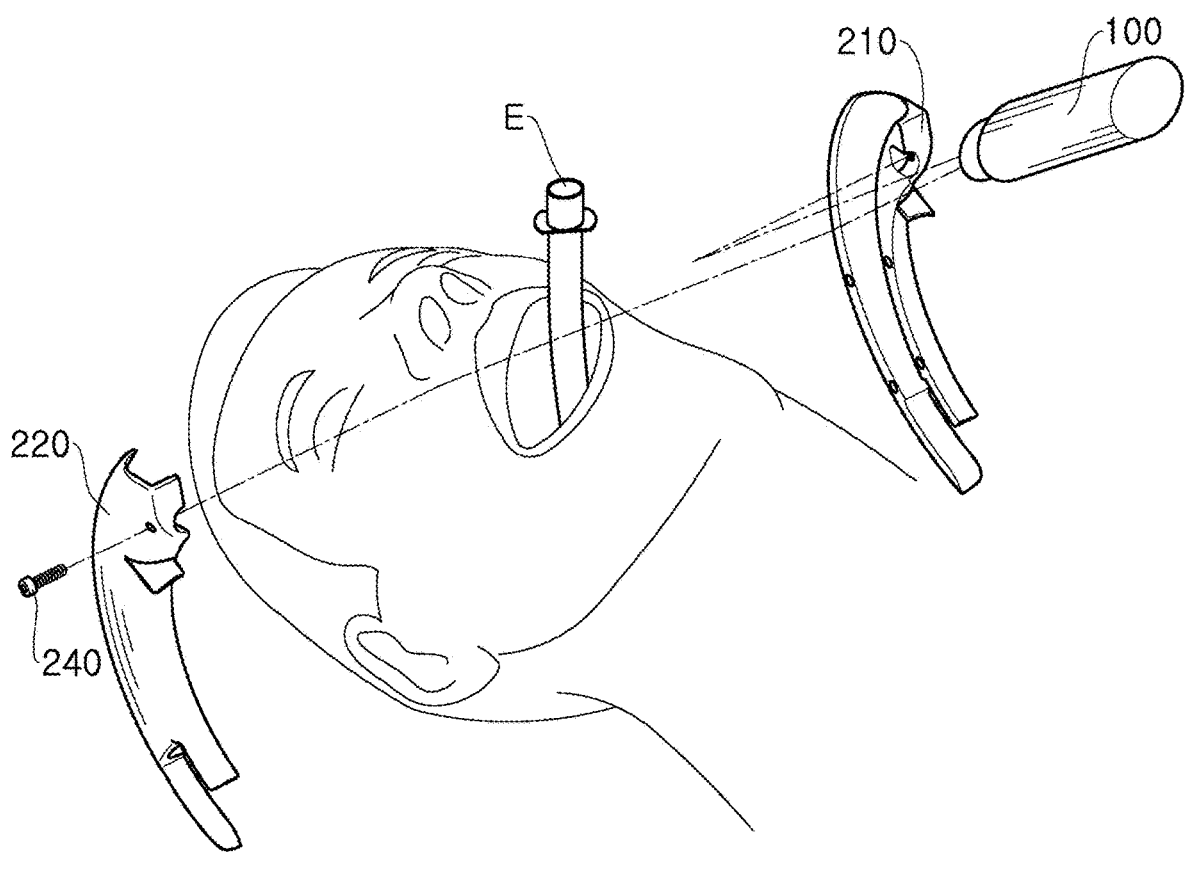
FIG. 2D is a schematic view illustrating a state where the E-tube is provided using the tracheal intubation guide apparatus according to the example of the present invention and then the tracheal intubation guide apparatus is disassembled.

FIG. 2A is a schematic view illustrating a state before the tracheal intubation guide apparatus according to the example of the present invention is provided to an operation subject. FIG. 2B is a schematic view illustrating a state where the tracheal intubation guide apparatus according to the example of the present invention is provided into an oral cavity of the operation subject. FIG. 2C is a schematic view illustrating a state where the tracheal intubation guide apparatus according to the example of the present invention is provided into the oral cavity of the operation subject and then an E-tube is provided through a tracheal intubation guide passage. FIG. 2D is a schematic view illustrating a state where the E-tube is provided using the tracheal intubation guide apparatus according to the example of the present invention and then the tracheal intubation guide apparatus is disassembled.

As illustrated in FIGS. 2A to 2C, the tracheal intubation guide apparatus 1000 is provided to the operation subject and then provided through the guide passage H.

As described above, the apparatus of the present invention is provided with the laryngeal cover clasps 213 and 223 protruding from the distal end of the case and the esophageal insertion prevention plates 215 and 225 protruding farther from the case than the laryngeal cover clasps 213 and 223. Thus, a path toward the esophagus is blocked, a tract is formed toward the trachea in advance.

As a result, structurally, the tip of the E-tube can be prevented from entering the esophagus and can be caused to enter the trachea. Consequently, in this state, simply pushing the E-tube into the guide passage H by an operator enables intubation into the trachea even in a blind state. Hence, an ETI attempt barrier to an operator such as a paramedic can be lowered, and the operator can use the apparatus without difficulties even in a hospital where securing the trachea is very important in an emergency room, an operating room, or the like.

As illustrated in FIG. 2D, the tracheal intubation guide apparatus 1000 can be easily disassembled and removed after the E-tube intubation.

In other words, as described above, the tracheal intubation guide apparatus 1000 of the present invention is not only easy to assemble but also easy to disassemble, since the first case body 210 forming the right half of the case and the second case body 220 forming the left half of the case are coupled to each other by the magnet M and the handle 100, the first case body 210, and the second case body 220 are coupled to each other by one screw 240. As a result, the tracheal intubation guide apparatus 1000 can be easily disassembled and removed after the E-tube intubation, thereby solving a problem of interference with performing of another treatment or the like.

On the other hand, the exemplary embodiments of the present invention include: the above-described tracheal intubation guide apparatus; and a manual for using the tracheal intubation guide apparatus (or instructions for instructing how to use the apparatus). The manual provided in the kit can include instructions for an operator to put and fix the tracheal intubation guide apparatus in an oral cavity of an operation subject, pass an endotracheal tube along the tracheal intubation guide passage of the tracheal intubation guide apparatus, and then decouple the first case body from the second case body of the tracheal intubation guide apparatus or the first case body, the second case body, and the handle from each other.

For example, to be more specifically described with reference to FIGS. 1B and 2D, the manual can include an instruction to unscrew the screw 240 to remove the handle 100 and then decouple the first case body 210 and the second case body 220 coupled to each other by the magnet from each other.

Additionally, the manual can further include an instruction to, for appropriate positioning of the tracheal intubation guide apparatus, place the tooth clasp on teeth of the operation subject to have the centerline of the tooth clasp located between the two teeth (31st tooth and 41st tooth) (refer to FIG. 3) at the center of the mandible of the operation subject.

With reference to the above-provided descriptions, those skilled in the art to which the present invention pertains can understand that the present invention can be realized as another embodiment without changing the technical idea or an essential feature of the present invention.

Hence, the above-described examples are to be construed to be provided as exemplary examples in every aspect and not to be provided for limiting the present invention to the examples. The scope of the present invention is represented by the claims to be described below rather than the above-described description of embodiments, and every modified or altered example derived from the meaning and the scope of the claims and the equivalent concept of the claims is to be construed to be included in the scope of the present invention.

INDUSTRIAL APPLICABILITY

The present invention enables an ETI attempt barrier to an operator can be lowered and the ETI can be easy to attempt in a situation where securing the trachea is important at an emergency scene, an emergency room, an operating room, an intensive care unit, or the like. In particular, a procedure of securing the trachea can be performed in a prehospital state.

The invention claimed is:

1. A tracheal intubation guide apparatus comprising:

a longitudinally curved cylindrical case capable of being inserted into an oral cavity, wherein the case has an endotracheal tube insertion hole on a proximal side, an endotracheal tube discharge hole on a distal side, and a longitudinally curved tracheal intubation guide passage connecting the endotracheal tube insertion hole and the endotracheal tube discharge hole, and a tooth clasp is provided on the proximal side of the case, wherein the case forms a downward curve from the proximal side to a center and an upward curve from the center to the distal side, wherein the case includes a first case body forming a right half of the case and a second case body forming a left half of the case, the first case body and the second case body being coupled by one or more magnets configured to allow coupling and decoupling, wherein the tooth clasp being positioned to have a centerline thereof located between a 31st tooth and a 41st tooth at a center of a mandible of an operation subject to place a distal exit of the guide passage immediately in front of an entrance of a trachea, wherein one side of the distal end of the case is provided with a laryngeal cover clasp protruding from the case, the laryngeal cover clasp being configured to push an epiglottis upward to expose the trachea, wherein the other side of the distal end of the case is provided with an esophageal insertion prevention plate protruding farther from the case than the laryngeal cover clasp to prevent insertion into the esophagus, and wherein the endotracheal tube discharge hole is located in an area between the laryngeal cover clasp and the esophageal insertion prevention plate, further comprising a handle;

wherein each of the first case body and the second case body includes a handle coupler positioned on a rear surface side of the tooth clasp; and wherein the handle, the first case body, and the second case body are fastened to be coupled to and decoupled from each other at the handle coupler by a single screw passing through the handle and engaging the handle couplers of the first and second case bodies.

2. A tracheal intubation guide kit comprising:

the tracheal intubation guide apparatus according to claim 1; and a manual for using the tracheal intubation guide apparatus, wherein the manual includes instructions for an operator to put and fix the tracheal intubation guide apparatus in an oral cavity of an operation subject, pass an endotracheal tube along the tracheal intubation guide passage of the tracheal intubation guide apparatus, and then decouple the first case body from the second case body of the tracheal intubation guide apparatus or the first case body, the second case body, and the handle from each other.

3. The tracheal intubation guide kit according to claim 2, wherein the tracheal intubation guide apparatus further includes the tooth clasp on the proximal side of the case, and wherein the manual further includes an instruction to place the tooth clasp on teeth of the operation subject to have the centerline of the tooth clasp located between the 31st tooth and the 41st tooth at a center of a mandible of the operation subject.

* * * * *